United States Patent [19]

Patierno et al.

[11] Patent Number: 5,696,092
[45] Date of Patent: Dec. 9, 1997

[54] METHODS AND COMPOSITIONS FOR INHIBITING METASTASIS OF EPITHELIAL CELL-DERIVED CANCERS

[75] Inventors: Steven R. Patierno, Falls Church, Va.; Michael Manyak, Chevy Chase, Md.

[73] Assignee: George Washington University, Washington, D.C.

[21] Appl. No.: 400,084

[22] Filed: Mar. 7, 1995

[51] Int. Cl.$^6$ .................................................. A61K 38/17
[52] U.S. Cl. ........................................ 514/21; 514/12
[58] Field of Search ............................... 530/350, 352, 530/359, 386, 395, 850, 851, 853; 514/7, 8, 12, 21

[56] References Cited

U.S. PATENT DOCUMENTS

| 5,266,562 | 11/1993 | Mukherjee et al. | 514/14 |
| 5,284,827 | 2/1994 | Maione et al. | 530/380 |
| 5,359,078 | 10/1994 | Kohn et al. | 548/265.8 |

FOREIGN PATENT DOCUMENTS

91/07187  5/1991  WIPO.

OTHER PUBLICATIONS

Leyton et al, "Recombinant human uteroglobin-like protein...". Proc. Amer. Assoc. Canc. Res. Mar. 1994, vol. 35, p. 280, Abstract No. 1675.
Manyak et al. Inhibition of Prostate Adenocarcinoma Invasion In Vitro By Uteroglobin-Like Protein. The Journal Of Urology. May 1994, vol. 151, No. 5, p. 368A, Abstract No. 564.
Hill, R.R., Chapter 11, *Metastasis*, pp. 178–195 in *The Basic Science of Oncology*, Tannock et al., Eds., McGraw–Hill, N.Y. (1992).
Aznavoorian et al., *Cancer*71: 1368–83 (1993).
Singh et al., *BBA*950: 329–337 (1988).
Miele et al., *Endocrine Reviews*8: 474–90 (1987).
Nieto et al., *Arch. Biochem. Biophys.*180: 82–92 (1977).
Mantile et al., *J. Biol. Chem.*26B: 20343–20351 (1993).
Miele et al., *J. Biol. Chem.*265: 6427–35 (1990).
Sambrook et al., Molecular Cloning: A Laboratory Manual, 2nd Ed., Cold Spring Harbor Laboratory Press, Cold Spring Harbor, N.Y. (1989), Cover and copyright pages only.
Arcone et al., *Eur. J. Biochem.*, 211: 347–55 (1993).
Cirino et al., *British J. Pharmacol.*, 108: 573–4 (1993).
Bastian et al., *J. Invest. Dermatol.*, 101: 359–63 (1993).
Merk Index, 11th Ed., Budavari et al., Merk & Co., Inc. Rahway, N.J. (1989), Cover and copyright pages only.
Goodman and Gilman's: The Pharmacological Bases of Therapeutics, 8th Ed., Gilman et al. Eds., Pergamon Press (1990), Cover and copyright pages only.
Remington's Pharmaceutical Sciences, 17th Ed., Mack Publishing Co., Easton, PA (1990), Cover and copyright pages only.
Cancer Therapy With Radiolabeled Antibodies, D.M. Goldenberg, Ed., CRC Press, Boca Raton, FL (1995), Cover and Copyright pages only.
Stone et al., *Int. J. Cancer*, 21: 274–281 (1978).

(List continued on next page.)

*Primary Examiner*—Jeffrey E. Russel
*Attorney, Agent, or Firm*—Gary M. Nath; Todd L. Juneau; Nath & Associates

[57] ABSTRACT

The present invention relates to methods and compositions that prevent or inhibit metastases of cancers of epithelial cell origin, especially human prostate cancers. A particular aspect of the invention relates to methods and compositions that inhibit arachidonic acid release in cells of these cancers and inhibit or prevent metastasis. In one aspect in this regard, the invention particularly relates to methods and compositions that inhibit phospholipase $A_2$ that mediates arachidonic acid release in the cancer cells. In a further aspect, the invention relates to methods and compositions wherein uteroglobin, uteroglobin muteins, peptide analogs of uteroglobins, lipocortins, lipocortin muteins and peptide analogs of lipocortins inhibit arachidonic acid release by cancer cells. In this regard, the invention relates especially to uteroglobins, particularly human uteroglobins.

8 Claims, 5 Drawing Sheets

OTHER PUBLICATIONS

Horoszewicz et al., *Cancer Res.*, 43: 1809–18 (1983).
Kaighn et al., *Invent. Urol.*, 17: 16–23 (1979).
Iizumi et al., *J. Urology*, 137: 1304–1306 (1987).
Albini et al., *Cancer Research*, 47: 3239–3245 (1987).
Leyton et al., *Cancer Research*, 54: 3696–3699 (1994).
Frandson et al., *Fibrinolysis*, 6 (Supp. 4): 71–76 (1992).
Monoclonal Antibodies–Production, Engineering and Clinical Applications, Ritter et al., Eds., Cambridge University Press, Cambridge, UK (1995).

METHODS AND COMPOSITIONS FOR INHIBITING METASTASIS OF EPITHELIAL CELL-DERIVED CANCERS

The present invention relates to methods and compositions that prevent or inhibit metastases of cancers of epithelial cell origin, especially human prostate cancers. A particular aspect of the invention relates to methods and compositions that inhibit arachidonic acid release in cells of these cancers and inhibit or prevent metastasis. In one aspect in this regard, the invention particularly relates to methods and compositions that inhibit phospholipase $A_2$ that mediates arachidonic acid release in the cancer cells. Compositions of the invention also particularly include those that contain uteroglobin, uteroglobin muteins, peptide analogs of uteroglobins, lipocortins, lipocortin muteins and peptide analogs of lipocortins that inhibit arachidonic acid release by cancer cells. In this regard, the invention relates especially to compositions that contain uteroglobin, particularly human uteroglobin. Further compositions of the invention include other types of active ingredients in combination with those that inhibit arachidonic acid release.

The invention also particularly relates to methods to prevent or inhibit metastases of human cancers of epithelial cell origin by administering the foregoing compositions. Especially in this regard the invention relates to methods using human uteroglobin to inhibit or prevent metastasis of human prostrate cancers.

Methods and compositions of the invention may be used by themselves and with other treatment modalities.

BACKGROUND OF THE INVENTION

Cancers develop from uncontrolled multiplication of cells. All cancers are life threatening. Even when cancer does not result in death, it is permanently debilitating, not only to the patient, but also to family, friends and co-workers. Too often, moreover, cancers prove fatal. The personal and public loss from this cluster of diseases, which cause an significant fraction of all premature deaths, is beyond estimation.

Although effective treatment modalities have been developed in a few cases, many cancers remain refractory to currently available therapies. Particularly difficult to treat are metastatic cancers, and there is a clear need for improved anti-metastatic agents and methods to treat metastatic cancers. Metastatic cancers originate as a primary tumor. Metastasis of the primary tumor produces secondary tumors and disseminated cancer.

It is well known that both primary and secondary tumors shed large numbers of cells. The shed cells can spread through the body. For instance, a primary tumor may damage the surrounding lymph or circulatory vessels, allowing entry of shed cells in the lymph or circulatory systems, and hastening their spread in the body. Moreover, shedding of cells by cancerous tumors increases during surgery and radiotherapy.

Most shed cells do not form new tumors. To do so such cells must surmount a series of physical and physiological barriers. In fact, a series of distinct events must occur for metastasis to occur. The primary tumor physically must (i) invade interstitial space of the primary tissue. In particular, it must (ii) penetrate the basement membrane of the tissue. For most metastases the tumor must damage the endothelial cell wall of lymphatic or vascular vessels to provide access to shed cells. Cells that enter the lymph or blood must (iii) survive the hemodynamic stress and host defenses in the circulation and, furthermore, (iv) lodge at a new site in the circulatory system, a process that apparently involves aggregated platelets. A cell then must (v) extravasate out of the vessel into the interstitial space. Finally, it must (vi) invade the interstitial space of the secondary organ and proliferate in the new location. Although the process of metastasis is physiologically complex, the overall pattern of metastasis is general to many types of cancers.

The metastatic process also clearly involves complex intracellular mechanisms that alter cancerous cells and their interactions with surrounding cells and tissues. For instance, cancerous cells are characterized by aberrant expression of adhesion proteins, enzymes that degrade matrix components, autocrine factors, ligand-responsive receptors, factors of angiogenesis and prostaglandins, to name a few. In particular, the signaling pathways that initiate tumor cell migration are among the least understood aspects of invasion and metastasis. Currently, it is thought that proliferation of many cancerous cells depends upon specific ligand-receptor interactions. Thus far, however, it has not been possible to use this paradigm, or other concepts of the underlying mechanisms of metastasis to develop a therapy that prevents or effectively inhibits metastasis of metastatic cancers.

The complexity of the processes involved in metastasis have made it particular difficult to develop effective treatments to inhibit or prevent the spread of metastatic cancer. Clearly, there remains a need for effective anti-metastatic compositions and methods.

SUMMARY OF THE INVENTION

It therefore is an object of the present invention to provide methods for inhibiting or preventing metastasis.

It is another aspect of the present invention to provide compositions for inhibiting or preventing metastasis.

In accomplishing the foregoing objects, there has been provided, in accordance with one aspect of the present invention, a method for preventing or inhibiting metastasis of a cancer of epithelial cell origin, comprising the step of administering to an organism suffering from a cancer of epithelial cell origin a compound that inhibits arachidonic acid release by cells of said cancer by a route and in an amount effective to inhibit or prevent metastasis of said tumor.

In a preferred embodiment of one aspect of the invention, the compound is an inhibitor of phospholipase $A_2$.

In particularly preferred embodiment of this aspect of the invention, the compound is a uteroglobin, a mutein of a uteroglobin, a peptide analog of a uteroglobin, a lipocortin, a mutein of a lipocortin or a peptide analog of a lipocortin. Especially highly preferred in this regard are methods wherein the compound is a uteroglobin, a mutein of a uteroglobin or a peptide analog of a uteroglobin. Particular, uteroglobin is preferred and human uteroglobin is particularly highly preferred.

In another regard, preferred embodiments of the present method are those used to treat a cancer of the prostate gland in a human patient.

In further preferred embodiments, the method is used in conjunction with another treatment. In this regard, preferred treatments include surgical intervention, radiation therapy, hormonal therapy, immunotherapy, chemotherapy or cryotherapy.

In accordance with another aspect of the present invention, there has been provided a pharmaceutical composition for inhibiting or preventing metastasis of a cancer of epithelial cell origin, comprising: (i) a compound that inhibits arachidonic acid release by cells of a tumor of epithelial cell origin in an organism and (ii) a carrier for effective therapeutic administration of said compound to said organism.

In certain preferred embodiments of the invention the compound is an inhibitor of phospholipase $A_2$. In particularly preferred embodiments the compound is a uteroglobin, a mutein of a uteroglobin, a peptide analog of a uteroglobin, a lipocortin, a mutein of a lipocortin or a peptide analog of a lipocortin. In especially preferred embodiments in this regard the compounds is a uteroglobin, a mutein of a uteroglobin or a peptide analog of a uteroglobin. Among these uteroglobins are very highly preferred, and human uteroglobins are among the most highly preferred compounds of the present invention.

Other objects, features and advantages of the invention will be apparent from the following detailed description. It should be understood, however, that the detailed description and the specific examples, while providing general and specific descriptions and indicating preferred embodiments of the invention, are given by way of illustration only. Various changes and modifications within the spirit and scope of the invention will become apparent to those skilled in the art from the detailed description and other aspects of the present disclosure.

GLOSSARY

Figure 1:
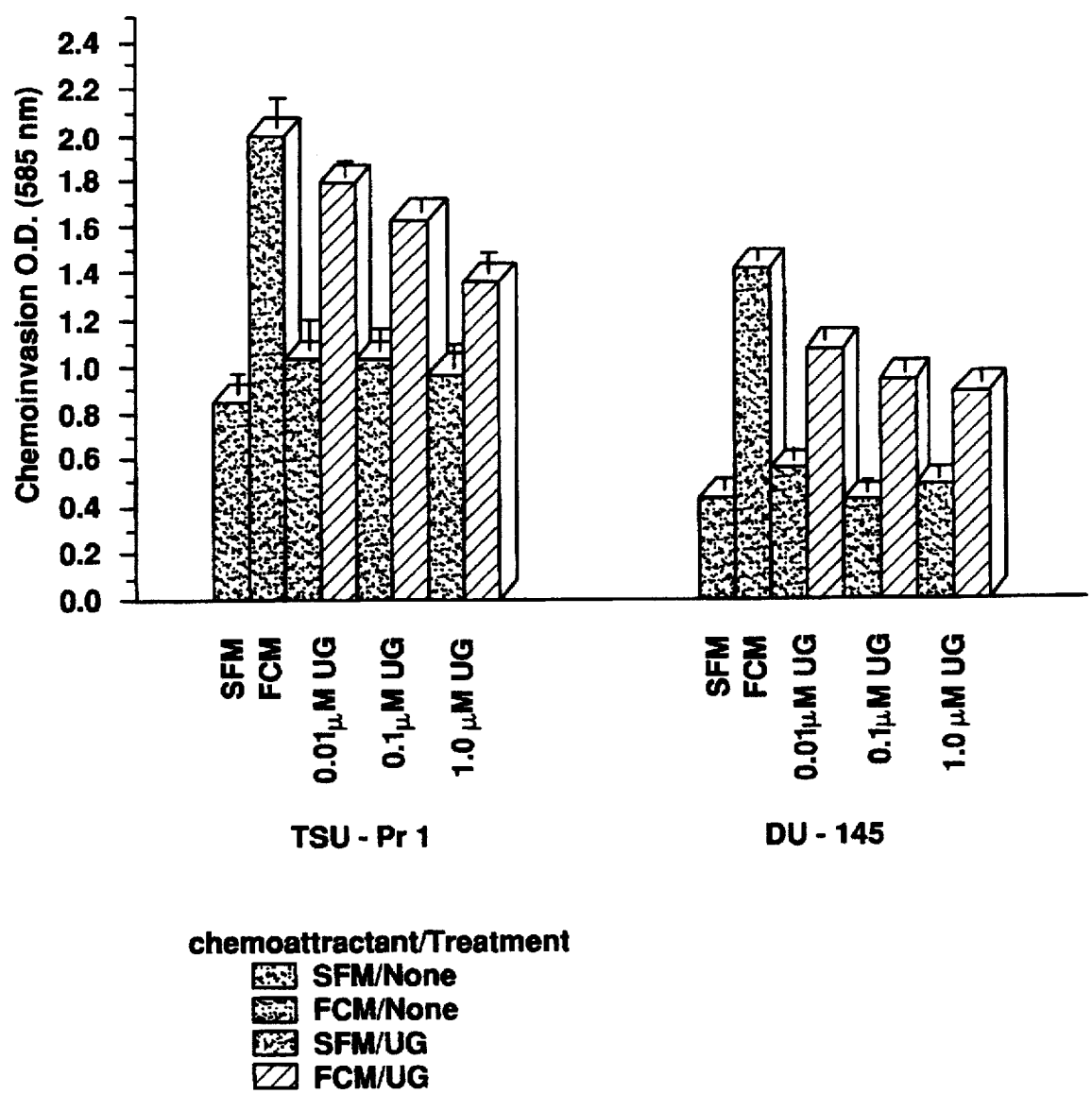
FIG. 1 is a bar chart showing the dose effect of uteroglobin on the invasiveness of cells of the TSU-Pr1 and DU-145 cell lines, epithelial cell lines derived from human prostate tumors. Both TSU-Pr1 and DU-145 cells are androgen independent. Cells were cultured in zero, 0.01, 0.1 and 1.0 uteroglobin for 24 hr. Invasiveness then was assayed by migration through filters coated with reconstituted basement membrane (RBM) in response to serum free or fibroblast conditioned media. Invading cells were stained with crystal violet, the dye was extracted and invasiveness was determined by measuring dye concentration by optical absorbance at 585 nm. Each point in the graph is the mean of triplicate cultures in three separate experiments, and the bars show the standard error of the mean.

The abbreviations and terms in the present disclosure are employed in contemplation of their fullest meaning consistent with the disclosed and claimed invention. The following brief explanations are entirely illustrative and neither exhaustively define nor limit the invention disclosed and claimed herein. The full meaning of the terms will be clear from an understanding of the invention based on contemplation of the disclosure as a whole in light of a full understanding of the pertinent arts.

METASTASIS: As set out in Hill, R. P., Chapter 11, *Metastasis*, pp178–195 in *The Basic Science of Oncology*, Tannock et al., Eds., McGraw-Hill, New York (1992), which is incorporated by reference herein in its entirety, metastasis is "The ability of cells of a cancer to disseminate and form new foci of growth at noncontiguous sites (i.e., to form metastases)".

Similarly, metastasis is described in Aznavoorian et al., *Cancer* 71: 1368–1383 (1993), which is incorporated by reference incorporated in its entirety, as "The transition from in situ tumor growth to metastatic disease is defined by the ability of tumor cells of the primary site to invade local tissues and to cross tissue barriers. . . . To initiate the metastatic process, carcinoma cells must first penetrate the epithelial basement membrane and then invade the interstitial stroma. . . . For distant metastases, intravasation requires tumor cell invasion of the subendothelial basement membrane that must also be negotiated during tumor cell extravasation. . . . The development of malignancy is also associated with tumor-induced angiogenesis [which] not only allows for expansion of the primary tumor, but also permits easy access to the vascular compartment due to defects in the basement membranes of newly formed vessels."

ARACHIDONIC ACID CASCADE: a series of enzymatic reactions that results in the production and release of arachidonic acid by a cell. The cascade is sensitive to ligand signals and arachidonic acid itself is an autocrine factor.

EPITHELIAL CELL ORIGIN: derived from an epithelial cell, of whatever tissue.

PLA: phospholipase A $PLA_2$: phospholipase $A_2$

INHIBITION: inhibition of metastasis may be measured by many parameters in accordance with the present invention and, for instance, may be assessed by delayed appearance of secondary tumors, slowed development of primary or secondary tumors, decreased occurrence of secondary tumors, slowed or decreased severity of secondary effects of disease, arrested tumor growth and regression of tumors, among others. In the extreme, complete inhibition, is referred to herein as prevention.

PREVENTION: in relation to metastasis, virtually complete inhibition, no metastasis if it had not occurred, no further metastasis if there had already been metastasis of a cancer. See INHIBITION.

UG: uteroglobin hUG: human uteroglobin

MUTEIN: An amino acid sequence variant of a protein. The variation in primary structure may include deletions, additions and substitutions. The substitutions may be conservative or non-conservative. The differences between the natural protein and the mutein generally conserve desired properties, mitigate or eliminate undesired properties and add desired or new properties. In the present invention the muteins generally are those that maintain or increase anti-metastatic activity. Particularly, uteroglobin muteins are amino acid sequence variants of uteroglobin that maintain or increase the anti-metastatic activity of uteroglobin.

PEPTIDE ANALOG: an oligo or polypeptide having an amino acid sequence of or related to a protein. Peptide analogs of the present invention are peptides that have anti-metastatic activity and an amino acid sequence the same as or similar to a region of an anti-metastatic protein, such as uteroglobin.

DU-145: an epithelial cell line derived from a human prostate tumor, which is androgen independent.

LNCaP: an epithelial cell line derived from a human prostate tumor, which is androgen sensitive. The LNCaP cell line was derived from a supraclavicular lymph node metastasis of a human prostate carcinoma. Cells of this line exhibit increased proliferation in response to androgen, in vitro, and they secrete prostate specific antigen (PSA), a marker of differentiated epithelial cells.

TSU-Pr1: an epithelial cell line derived from a human prostate tumor, which is androgen independent.

PC3-M: an epithelial cell line derived from a human prostate tumor, which is androgen independent.

FCM: fibroblast conditioned media

RBM: reconstituted basement membrane. A multicomponent matrix approximating the molecular composition of the intracellular tissue matrix and the epithelial cell basement membrane. Preparations for preparing RBM are well known and are available from commercial suppliers.

SFM: Serum free medium

PSA: Prostate specific antigen.

DETAILED DESCRIPTION OF THE INVENTION

Notwithstanding past failures to develop anti-metastatic treatments, the present invention provides compounds and compositions for inhibiting cancer metastases and methods for administering the compounds and compositions to inhibit or prevent metastasis of a tumor of epithelial cell origin in an organism.

ANTI-METASTATIC AGENTS OF THE COMPOSITIONS AND METHODS OF THE INVENTION

In accordance with the methods and compositions of the invention, compounds that inhibit arachidonic acid release by cells of a tumor of epithelial cell origin in an organism are administered by a route and in an amount effective to prevent or inhibit metastasis of the tumor.

Inhibitors of arachidonic acid release

Without being limited to any theory of the invention, applicants note that arachidonic acid is a substrate in the synthetic pathway of eicosanoids in cells. Various eicosanoids play a role in stimulating or inhibiting shape, attachment, motility and proliferation of cells. In some aspects of the invention, inhibiting arachidonic acid release in cells of tumors of epithelial cell origin inhibits or extinguishes metastatic potential.

Inhibitors of phospholipase $A_2$

Compounds that inhibit phospholipase $A_2$ ($PLA_2$) are preferred compounds of the present invention. $PLA_2$ is a membrane signaling enzyme of the arachidonic acid cascade, the series of enzymes, substrates, products and co-factors involved in the production and secretion of arachidonic acid, and it generally would be appreciated that inhibitors of $PLA_2$ activity generally will inhibit release of arachidonic acid. Notably, $PLA_2$ has been associated with processes of inflammation, rather than tumorigenesis or metastasis, and it has been suggested as a target for the control of chronic inflammation, but not as a target for developing an anti-metastatic agent. Nevertheless, the present provides compositions and methods of $PLA_2$ inhibitors for inhibiting metastasis of tumors of epithelial cell origin. The formulation and use of these compounds in the invention is illustrated by reference to the preferred embodiments discussed below.

Especially preferred among $PLA_2$ inhibitors are lipocortins, muteins of lipocortins, peptide analogs of lipocortins and uteroglobins, muteins of uteroglobins and peptide analogs of uteroglobin. Uteroglobins, muteins of uteroglobins and peptide analogs of uteroglobin are particularly preferred. Most particularly preferred are uteroglobins, and among these human uteroglobin is very especially preferred. The discussion below, directed to uteroglobin, particularly human uteroglobin, illustrates the invention is this regard.

Uteroglobin

Uteroglobin, also called blastokinin, was first discovered as a major protein component of the rabbit uterine fluid during early pregnancy. The human counterpart to rabbit uteroglobin was first found in nonciliated Clara cells in the distal bronchiole airway and was originally designated CC10. Uteroglobin also has been detected in humans in the uterus, respiratory tract, and prostate gland, by immunohistochemical methods.

The complementary DNA for human uteroglobin (CC10) has been cloned and its sequence has been determined, as reported in Singh et al., *BBA* 950: 329–337 (1988), incorporated by reference herein in its entirety.

Uteroglobin has been purified to homogeneity by at least two groups and it has been structurally and functionally characterized in considerable detail. In brief, uteroglobin occurs in rabbits as a dimer of two identical chains. The monomers are 70 amino acids long. The are arranged antiparallel to one another in the dimer. Also, in the dimer they are covalently linked by two symmetrical disulfide bonds, which formed between 'Cys-3' and "Cys-69" and, reciprocally, between 'Cys-69' and "Cys-3" (where ' designates one chain in the dimer and " designates the other chain). Each monomer chain contains four α-helical segments and a β-turn, the later at Lys-26 to Gln-29. The structure, function and activities of uteroglobin is reviewed, for instance, by Miele et al., *Endocrine Reviews* 8: 474–490 (1987), which is incorporated by reference herein in its entirety.

Uteroglobin inhibits the activity of $PLA_2$, as shown by in vitro assays. Generally, it has been thought to have immunomodulatory or anti-inflammatory activities, or both, that act to protect the wet epithelia of organs that communicate with the external environment. Uteroglobin expression is steroid-sensitive and its secretion in the endometrium has been shown to be stimulated by progesterone. Uteroglobin also has been reported to have an anti-chemotactic effect on neutrophils and monocytes. Uteroglobin has not been seen as playing any role in cancer or metastasis. Thus, it was surprising to find that uteroglobin, in accordance with the present invention, can be used to inhibit or prevent metastasis of a tumor of epithelial cell origin in an organism.

Without being bound to any theory of the mechanism by which uteroglobin inhibits metastasis, it appears, as the Examples show, that the inhibitory action of uteroglobin on metastasis results from inhibition of $PLA_2$ activity and inhibition of arachidonic acid release by the tumor cells.

Any uteroglobin may be useful in the invention that inhibits arachidonic acid release or $PLA_2$ activity that inhibits or prevents metastasis of a tumor of epithelial cell origin.

Uteroglobins for use in the invention may be recovered from natural sources, it may be made by recombinant means, it may be produced by chemical techniques, it may be made by semi-synthetic methods or it may be obtained by a combination of techniques.

Methods for purifying uteroglobin to homogeneity from a natural source have been described in Nieto et al., *Arch. Biochem. Biophys.* 180: 80–92 (1977), which is herein incorporated by reference in its entirety.

The most highly preferred uteroglobin for use in the invention at the present time is human uteroglobin. Preferably, human uteroglobin for use in the invention is made by expression of a cloned gene in a host cell in culture or in an animal. Techniques for expressing uteroglobin are well known to those of skill in the art.

Moreover, a cDNA encoding human uteroglobin has been isolated, sequenced and expressed in cells in culture. Methods for expressing cloned DNAs that encode uteroglobin are described specifically with regard to human uteroglobin in Mantile et al., *J. Biol Chem.* 268: 20343–20351 (1993) and Miele et al., *J. Biol. Chem.* 265: 6427–6435 (1990), which, as noted below, are incorporated by reference herein in their entirety.

Techniques for obtaining, manipulating and expressing cloned genes to obtain uteroglobin for use in the present invention are well known to those of skill in the art and are described in protocol-like detail in a variety of laboratory manuals. For instance, such methods are set forth in Sambrook et al., MOLECULAR CLONING: A LABORATORY MANUAL, 2ND Ed., Cold Spring Harbor Laboratory Press, Cold Spring Harbor, N.Y. (1989), the entirety of which is herein incorporated by reference.

Lipocortins

Lipocortin proteins also are known as annexins, and are well known to the art. They generally have been characterized as calcium-dependent phospholipid-binding proteins. For instance, Arcone et al., *Eur. J. Biochem,* 211: 347–355 (1993), incorporated by reference herein in its entirety, reports on the structure of human lipocortin 1 and the expression of the active protein using an expression vector in *E. coli.*

Lipocortins have been implicated in the mechanism of anti-inflammatory activity of glucocorticosteroids. Furthermore, anti-inflammatory activity is associated with the amino-terminal end of human lipocortin 1, as shown by the activity of acylated polypeptide corresponding to human lipoprotein residues 2–26 synthesized and characterized by Cirino et al., *J. Pharmacol.* 108: 573–4 (1993), which is incorporated by reference herein in its entirety.

According to one hypothesis, lipocortins mediate a glucocorticosteroid-dependent inhibition of phospholipase $A_2$. Some studies support a "substrate-depletion" mechanism of phospholipase $A_2$ inhibition, as reported by Bastian et al., *J. Invest. Dermatol.* 101: 359–63 (1993), for instance, which is incorporated by reference herein in its entirety.

The studies have focused on the intermediary role of lipocortins in the anti-inflammatory response to glucocorticosteroids, however, and a role for the proteins in metastasis was unknown.

In accordance with one aspect of the present invention, lipocortins may be used to inhibit or present metastasis of tumors of epithelial cell origin. The methods of using lipocortins, and the compositions of lipocortins, in accordance with the present invention, will be understood by reference to the discussion elsewhere herein, particularly the disclosure relating to uteroglobin and to prostate cancers.

Lipocortins generally may be used in accordance with this aspect of the present invention. Preferred lipocortins have a high therapeutic effect and low incidence of deleterious side effects. Particularly preferred lipocortins are those of human origin. Human lipocortin 1 is among those particularly preferred.

Muteins and peptide analogs of lipocortins and uteroglobins

Techniques such as those described in the foregoing manual can be used to make variants and analogs of uteroglobin and other proteins useful in the invention. Recombinant DNA methods, chemical synthetic methods, enzymatic methods and mixed methods for making, altering and utilizing muteins and peptide analogs are well known and are described here only briefly to illustrate their applicability to the present invention.

Muteins

It will be appreciated by those of skill that cloned genes readily can be manipulated to alter the amino acid sequence of a protein. The cloned gene for human uteroglobin can be manipulated by a variety of well known techniques for in vitro mutagenesis, among others, to produce variants of the naturally occurring human protein, herein referred to as muteins, that may be used in accordance with the invention.

The variation in primary structure of muteins of lipocortins or uteroglobins useful in the invention, for instance, may include deletions, additions and substitutions. The substitutions may be conservative or non-conservative. The differences between the natural protein and the mutein generally conserve desired properties, mitigate or eliminate undesired properties and add desired or new properties. In the present invention the muteins generally are those that maintain or increase anti-metastatic activity. Particularly, uteroglobin muteins are amino acid sequence variants of uteroglobin that maintain or increase the anti-metastatic activity of uteroglobin.

Peptide analogs

Similarly, techniques for making small, oligopeptides, and polypeptide, that exhibit activity of larger proteins from which they are derived (in primary sequence) are well known and have become routine in the art. Thus, peptide analogs of proteins of the invention, such as peptide analogs of lipocortin and uteroglobin that exhibit anti-metastatic activity also are useful in the invention.

COMPOSITIONS

Any non-toxic, inert and effective carrier may be used to formulate compositions of the present invention. Well known carriers used to formulate other therapeutic compounds for administration to humans particularly will be useful in the compositions of the present invention. Pharmaceutically acceptable carriers, excipients and diluents in this regard are well known to those of skill, such as those described in the MERCK INDEX, 11th Ed., Budavari et al., Eds., Merck & Co., Inc., Rahway, N.J. (1989), which is incorporated by reference herein in its entirety. Examples of such useful pharmaceutically acceptable excipients, carriers and diluents include distilled water, physiological saline, Ringer's solution, dextrose solution, Hank's solution and DMSO, which are among those preferred for use in the present invention.

In particular, for instance Mantile et al., *J. Biol Chem.* 268.: 20343–20351 (1993), incorporated by reference hereinabove, report on sterile formulated, lyophilized uteroglobin that may be useful in preparing uteroglobin compositions of the invention.

CANCERS

Methods and compositions of the present invention may be applied to the treatment of a variety of cancers of epithelial cell origin. Among these are metastatic cancers of breast, lung, colon, bladder, prostate, gastrointestinal track, endometrium, tracheal-bronchial tract, pancreas, liver, uterus, nasopharynges and the skin. An especially preferred target is prostate cancer of epithelial cell origin.

The following detailed discussion of prostate cancers is provided in illustration of the compositions and methods of the invention not only as to prostate cancers, but also other cancers that may be treated in analogous or identical fashion, in accordance with the present invention.

Adenocarcinoma of the prostate is one of the most common malignancies. It is estimated that 240,000 new cases of prostate cancer will be diagnosed in the United States in 1995, and that it will cause more than 50,000 deaths during the year. In fact, prostate adenocarcinoma is the second leading cause of cancer-related mortality in the United States.

With prostate cancer, as with all solid tumors, it is the metastatic encroachment of the tumor on other vital function that causes the demise of the patient. Approximately 10% of patients are diagnosed initially with metastatic disease. Ultimately, 30-40% of patients with this cancer will develop metastatic disease. Once metastasis occurs there is a the cancer follows a relentless progression.

Invasion is a prerequisite for migration of tumor cells in connective tissue stroma and basement membranes form the major physical barriers to the migration process. Invasion of the local extracellular matrix (ECM) by tumor cells thus can be marked as the first step in metastasis. The sequential biochemical mechanism first involves cell attachment to specific components of ECM followed by a progressive cascade of proteolytic dissolution. Prostate cancers which grow to a critical size exhibit extracapsular invasion and metastasize to specific anatomical sites apparently in response to stromal cell secretory proteins which are necessary for their growth and proliferation. Invasive migration of tumor cells within the prostate gland may occur as a function of chemokinesis along anatomical paths of least resistance which include the perineural duct. Further establishment of metastasis relies upon successful penetration of the circulatory or lymphatic system, and vessel extravasation at the secondary organ which for prostate cancer is frequently bone tissue. Nearly all of these steps, including attachment, matrix degradation and migration, can be modeled experimentally in vitro by measuring invasion of a reconstituted basement membrane (RBM) barrier in response to fibroblast-conditioned medium (FCM) used as a chemo-attractant.

In vivo prostate tumor cells respond primarily to stromal cell (fibroblast) secretory proteins for their growth and proliferation. Applicants' have modeled prostate tumor cell extracapsular invasiveness using RBM which selects for cells that have attached to the RBM, degraded the RBM enzymatically, and cells finally migrated through the filter towards FCM used as a chemo-attractant. These events are consistent with the important in vivo steps in the metastatic spread of tumor cells through the basement membrane.

Prostate tumors frequently initially metastasize to regional lymph nodes, having disseminated through the lymphatic circulation. They also spread to other sites through the vascular system, which is extensively interconnected to the lymphatics. The final site of formation of metastasis is a function of a number of parameters, including: (i) the first capillary bed encountered by blood vessels draining the tumor, and (ii) organ preference of the tumor cells with respect to characteristics of specific tissues that nurture attachment and growth of tumor cells with metastatic potential.

Metastatic potential of prostate cancers of epithelial cells origin can be inhibited by compositions and methods of the invention. In particular, metastasis of these cancers can be inhibited by human uteroglobin, as shown by the examples set out herein below.

ROUTE OF ADMINISTRATION

Therapeutic treatment with uteroglobin can utilize any type of administration including topical and invasive means. Generally, at the present time, invasive techniques are preferred. Administration may be intravenous, intraperitoneal, intramuscular or directly in tumors, among others.

Administration also may be by non-invasive means. For instance, administration may be by oral, intranasal or transdermal routes.

In addition, administration may be by a single dose, it may be repeated at intervals or it may be by continuous infusion. Where continuous infusion is preferred, pump means often will be particularly preferred for administration. Especially, subcutaneous pump means may be preferred in this regard.

Since uteroglobin is small, easily diffusible, and relatively stable it is well suited to long-term continuous administration, such as by perfusion pump. Also, it may be desirable to administered uteroglobin and other agents of the present invention by intramuscular self-injection on a regular basis.

Compositions and methods of the invention also may utilize controlled release technology. Thus, for example, uteroglobin may be incorporated into a hydrophobic polymer matrix for controlled release over a period of days. Such controlled release films are well known to the art. Examples of polymers commonly employed for this purpose that may be used in the present invention include nondegradable ethylene-vinyl acetate copolymer and degradable lactic acid-glycolic acid copolymers. Certain hydrogels such as poly(hydroxyethylmethacrylate) or poly (vinylalcohol) also may be useful, but for shorter release cycles then the other polymer releases systems, such as those mentioned above.

DOSE

The quantity of the active agent for effective therapy will depend upon a variety of factors, including the type of cancer, means of administration, physiological state of the patient, other medications administered, and other factors.

Treatment dosages generally may be titrated to optimize safety and efficacy. Typically, dosage-effect relationships from in vitro initially can provide useful guidance on the proper doses for patient administration. Studies in animal models also generally may be used for guidance regarding effective dosages for treatment of metastatic cancers in accordance with the present invention.

These considerations, as well as effective formulations and administration procedures are well known in the art and are described in standard textbooks, such as GOODMAN AND GILMAN'S: THE PHARMACOLOGICAL BASES OF THERAPEUTICS, 8th Ed., Gilman et al. Eds. Pergamon Press (1990) and REMINGTON'S PHARMACEUTICAL SCIENCES, 17th Ed., Mack Publishing Co., Easton, Pa. (1990), both of which are incorporated by reference herein in their entirety.

Typical therapeutic doses will be about 0.1 to 1.0 mg/kg of body weight of pure uteroglobin. The dose may be adjusted to attain, initially, a blood level of about 0.1 µM.

A particular formulation of the invention uses a lyophilized form of uteroglobin, in accordance with well known techniques. For instance, 1 to 100 mg of uteroglobin may be lyophilized in individual vials, together with carrier and buffer compound, for instance, mannitol and sodium phosphate. The uteroglobin may be reconstituted in the vials with bacteriostatic water and then administered, as described elsewhere herein.

ADMINISTRATION REGIMEN

Any effective treatment regimen can be utilized and readily determined and repeated as necessary to affect treatment.

In clinical practice, the compositions containing uteroglobin or recombinant uteroglobin alone or in combination with other therapeutic agents are administered in specific cycles until a response is obtained.

For patients who initially present without metastatic disease, Uteroglobin-based drugs are used as an immediate initial therapy prior to surgery and radiation therapy, and as a continuous post-treatment therapy in patients at risk for recurrence or metastasis (based upon high PSA, high Gleason's score, locally extensive disease, and/or pathological evidence of tumor invasion in the surgical specimen). The goal in these patients is to decrease the escape of potentially metastatic cells from the primary tumor during surgery or radiotherapy, decrease the escape of tumor cells from undetectable residual primary tumor, decrease tumor cell attachment to the interior vessel wall, decrease the migration of tumor cells out of the vessel, and decrease invasion into the interstitial spaces of the distal organ.

For patients who initially present with metastatic disease, Uteroglobin-based drugs are used as a continuous supplement to, or possible as a replacement for hormonal ablation. The goal in these patients is to slow tumor cell escape from both the untreated primary tumor and from the existing metastatic lesions in order to slow the progressive encroachment of further metastases.

In addition, the invention may be particularly efficacious during post-surgical recovery, where the present compositions and methods may be particularly effective in lessening the chances of recurrence of a tumor engendered by shed cells that cannot be removed by surgical intervention.

COMBINED WITH OTHER TREATMENTS

Uteroglobin may be used in conjunction with other treatment modalities. Other common treatment modalities are discussed below specifically by reference to prostate cancer. It will be appreciated that similar consideration will apply to treatment of other metastatic cancers. The present invention may be used in conjunction with any current or future therapy.

Surgery and Radiation

In general, surgery and radiation therapy are employed as potentially curative therapies for patients under 70 years of age who present with clinically localized disease and are expected to live at least 10 years. Neither treatment modality has a significant role in the management of metastatic diseases, and neither treatment is generally performed if metastasis is present at initial diagnosis.

Approximately 70% of newly diagnosed prostate cancer patients fall into this category. Approximately 90% of these patients (63% of total patients) undergo surgery, while approximately 10% of these patients (7% of total patients) undergo radiation therapy.

Histopathological examination of surgical specimens reveals that approximately 63% of patients undergoing surgery (40% of total patients) have locally extensive tumors or regional (lymph node) metastasis that was undetected at initial diagnosis. These patients are at a significantly greater risk of recurrence or metastasis. Approximately 40% of these patients will actually develop recurrence or metastasis within 5 years after surgery. Results after radiation are even less encouraging. Approximately 80% of patients who have undergone radiation as their primary therapy have disease persistence or develop recurrence or metastasis within 5 years after treatment.

Currently, most of these surgical and radiotherapy patients generally do not receive any immediate follow-up therapy. Rather, they are monitored frequently for elevated Prostate Specific Antigen ("PSA"), which is the primary indicator of recurrence or metastasis. Thus, there is considerable opportunity to use the present invention in conjunction with surgical intervention.

Hormonal Therapy

Hormonal ablation is the most effective palliative treatment for the 10% of patients presenting with metastatic disease at initial diagnosis. Hormonal ablation by medication and/or orchiectomy is used to block hormones that support the further growth and metastasis of prostate cancer. With time, both the primary and metastatic tumors of virtually all of these patients become hormone-independent and resistant to therapy. Approximately 50% of patients presenting with metastatic disease die within 3 years after initial diagnosis, and 75% of such patients die within 5 years after diagnosis.

In this regard it may be worth noting that the natural uteroglobin gene is dependent upon hormones for expression, and hormonal ablation may decrease expression of the endogenous uteroglobin gene, both in tumor cells and surround normal tissue. This uteroglobin-deficient state could render the patient more susceptible to successful metastasis. Continuous supplementation with Uteroglobin-based drugs are used to prevent or reverse this potentially metastasis-permissive state.

Chemotherapy

Chemotherapy has been more successful with some cancers than with others. It is likely that the combination of chemotherapy with therapies of the present invention in some case will be synergistic. However, chemotherapy currently has little effect on prostate cancer and is generally reserved as a last resort, with dismal results. For this type of cancer the opportunity to combine chemotherapy with methods and compositions of the invention will be rare.

Immunotherapy

The present invention may be used in conjunction with immunotherapies, as well as other treatment modalities. Not only may the methods and compositions herein disclosed be used with the increasing variety of immunological reagents now being tested or used to treat cancer, but it also may be used with those that come into practice in the future. The present invention thus may be used with immunotherapies based on polyclonal or monoclonal antibody-derived reagents, for instance. Monoclonal antibody-based reagents are among those most highly preferred in this regard. Such reagents are well known and are described in, for instance, Ritter MONOCLONAL ANTIBODIES—PRODUCTION, ENGINEERING AND CLINICAL APPLICATIONS, Ritter et al., Eds., Cambridge University Press, Cambridge, UK (1995), which is incorporated by reference herein in its entirety. Radiolabeled monoclonal antibodies for cancer therapy, in particular, also are well known and are described in, for instance, CANCER THERAPY WITH RADIOLABELED ANTIBODIES, D. M. Goldenberg, Ed., CRC Press, Boca Raton, Fla. (1995), which is incorporated by reference herein in its entirety.

Cryotherapy

Cryotherapy recently has been applied to the treatment of some cancers. Methods and compositions of the present invention also could be used in conjunction with an effective therapy of this type.

COMPOSITIONS CONTAINING COMPOUNDS OF THE INVENTION IN COMBINATION WITH OTHER ACTIVE AGENTS

According to another aspect of the invention, pharmaceutical compositions of matter useful for inhibiting cancer metastases are provided that contain, in addition to the aforementioned compounds, an additional therapeutic agent. Such agents may be chemotherapeutic agents, ablation or other therapeutic hormones, antineoplastic agents, monoclonal antibodies useful against cancers and angiogenesis inhibitors. The following discussion highlights some agents in this respect, which are illustrative, not limitative. A wide variety of other effective agents also may be used.

Among hormones which may be used in combination with the present invention diethylstilbestrol (DES), leuprolide, flutamide, cyproterone acetate, ketoconazole and amino glutethimide are preferred. Among antineoplastic and anticancer agents that may be used in combination with the invention 5-fluorouracil, vinblastine sulfate, extramustine phosphate, suramin and strontium-89 are preferred.

Among the monoclonal antibodies that may be used in combination with the invention CYT356 is preferred.

The present invention is further described by reference to the following, illustrative examples.

EXAMPLE 1

Preparation of human uteroglobin by gene expression

Human uteroglobin was purified from *E. coli* cells expressing a full-length cDNA. The methods for obtaining the cDNA, constructing it into a vector for expression in host, expressing the construct and purifying the protein all involve art routine techniques. Such methods are described specifically with regard to human uteroglobin in Singh et al., *BBA* 950: 329–337 (1988), Mantile et al., *J. Biol Chem.* 268: 20343–20351 (1993) and Miele et al., *J. Biol. Chem.* 265: 6427–6435 (1990), which are incorporated by reference herein in their entirety.

Briefly, in the present illustrative example, which followed the techniques set out in the foregoing references, a clone containing a full-length cDNA encoding human uteroglobin in the well known vector pGEM4Z was digested with PstI. (pGEM4Z may be obtained from Promega, Inc.) The digestion freed a 340-base pair fragment containing all of the cDNA and 53 nucleotides of the pGEM4Z polylinker. The fragment was purified by preparative by gel electrophoresis in low melting temperature agarose. The purified fragment was ligated into the PstI site of the expression vector pLD101, downstream of an inducible promoter. The ligation and subsequent cloning produced the plasmid pGEL101. This construct was introduced into *E. coli* strain BL21(DE3) cells for expression of uteroglobin protein. For expression, bacteria were cultured and then induced for uteroglobin expression by making the media 0.45 mM in IPTG (isopropyl-1-thio-D-galactopyranoside). After appropriate further incubation the cells were collected and then lysed, Uteroglobin then was purified from the lysed cells using standard methods of size exclusion and ion exchange chromatography.

EXAMPLE 2

Cells for assays of metastatic potential

The cell lines used in the illustrative embodiments herein discussed are well known and readily available. The four cell lines of the present examples all were derived from human prostate cancer and are of epithelial cell origin. TSU-Pr1, DU-145 and PC3-M are androgen-independent. LNCaP is androgen-sensitive.

DU-145 is described in Stone et al., *Int. J. Cancer* 21: 274–281 (1978), which is incorporated herein by reference in its entirety. The cell is available from a variety of sources including, for instance, the American Type Culture Collection (Rockville, Md.).

LNCaP is described in Horoszewicz et al., *Cancer Res.* 43: 1809–1818 (1983), which is herein incorporated by reference in its entirety. This cell line may be obtained from, for instance, from American Type Culture Collection (Rockville, Md.).

PC3-M is described in Kaighn et al., *Invent. Urol.* 11: 16–23 (1976) which is herein incorporated by reference in its entirety.

TSU-Pr1 is described in Hzumi et al., *J. Urology* 137: 1304–1306 (1987) which is incorporated by reference in its entirety.

Cells of each line were grown and maintained in monolayer culture in αMEM (minimal essential medium) supplemented with glutamine, 10% fetal bovine serum, penicillin (100 units/ml) and streptomycin (100 (g/ml). Cultures were incubated at 37° C. in 5% $CO_2$/95% air. Media was replaced every second day.

EXAMPLE 3

General assay for invasiveness of cells

1. Culture

As described briefly below, invasiveness of cells was assayed by the methods described in Albini et al., *Cancer Research* 47: 3239–3245 (1987), which is incorporated herein by reference in its entirety. Invasiveness assays and other methods for assessing anti-metastatic affects, as discussed herein below are described in Leyton et al., *Cancer Research* 54: 3696–3699 (1994) which is incorporated by reference herein in its entirety.

Cells in logarithmic phase were detached from the growth surface by brief exposure to 0.25% trypsin, 0.25% EDTA, collected and centrifuged at 800×g for 5 min. The pellet was resuspended in SF medium, counted and seeded into 6 mm dishes, $1.5 \times 10^6$ cells per dish. The cells then were incubated for 24 hr in media containing zero, 0.01, 0.1 and 1.0 µM uteroglobin. After the incubation cells were gently collected using a rubber policeman and assayed for invasiveness.

Fibroblast conditioned media (FCM) served as a chemoattractant to stimulate invasion. It was prepared by culturing proliferative 3T3 cells for 24 hr. in SF medium and then collecting the media, free of cells.

Invasiveness was measured using a polycarbonate membrane precoated with a reconstituted basement membrane. RBMs are well known. For example, Albini et al., supra describes RBM of the type employed for these experiments.

Assays were performed in blind-well Boyden chambers. The lower compartment of each chamber was filled with 220

µl of FCM, as chemo-attractant, or 220 µl serum-free media, as control for basal invasiveness. A polycarbonate membrane (12-µm pore size), coated with 25 µg/50 µl RBM, was placed over the lower compartment. Tumor cells for assay were added to the upper compartment, $3.0 \times 10^5$ cells per well, and the chambers then were incubated at 37° C. for 6 hr.

(Reconstituted basement membrane preparations for use in accordance with the foregoing assay are readily available from numerous commercial suppliers. One suitable example membrane in this regard is "MATRIGEL" sold by Collaborative Biomedical Products of Bedford, Mass.)

2. Quantitation

Invasive activity was measured by the number of cells that penetrated the RBM, as determined by a technique involving crystal violet staining developed for use with the Boyden cheer. The technique is well known and is described, for instance, in Frandson et al., *Fibrinolysis* 6(Supp4): 71–76 (1992).

The RBM-coated membrane was removed from each chamber at the end of the incubation period. The filters were down pinned to a wax plate, keeping the surface with the invading cells upward. The cells were stained on the filters with 0.5% crystal violet in 25% methanol for 10 minutes. Then, the filters were rinsed in distilled water, four times or until crystal violet no longer leached into the wash water. After the wash, the surface of each filter that had been in contact with the wax plate was carefully wiped clean with a moist cotton swab to remove nonmigrating cells. Then the filters were placed in a 24-well cluster plate and dried overnight.

Crystal violet in the invading cells on each filter was extracted twice for 10 minutes into 500 µl aliquots of 0.1M sodium citrate, 50% ethanol. Crystal violet in the extract was analyzed for absorbance at 585 nm using a standard spectrometer.

3. Analyses

Assays were carried out in triplicate for each data point.

Variance between control and test groups were analyzed for significance using the standard repeated measures test for analysis of variance. $P<0.01$ generally was considered indicative of a significant effect, with exceptions, as noted elsewhere herein.

EXAMPLE 4

Correlation of optical density with cell counts, and assay of basal invasiveness To calibrate optical density of the crystal violet extracts against the number of migrating cells on filters, cells were counted, seeded at known densities on filters, incubated to allow attachment and washed. One set of a duplicate set of plate was used for cell counting. The other set was used for staining. For counting, cells were released from the filters by mild trypsinization and then counted using an automated cell counter. For staining, after washing, the cells were stained and crystal violet stain then was extracted from the stained cells. The optical densities of the extracts were measured by standard spectroscopy. Optical densities then were matched to the number of cells attached to the filter determined by direct counting.

In accordance with the foregoing, several densities of DU-145 cells were seeded into the top chamber of the Boyden jars. The results are shown in Table I, which sets out the number of cells migrating to the lower face of the filters as a function of the number of cells seeded in the upper chamber. The number of cells migrating to the lower filter surface also is set out as a percentage of the total number of cells seeded in the top chamber. The data in the Table is the mean of triplicate determinations for each condition, and the indicated variance is the standard error of the mean.

At cell seedings greater than $2\times10^5$ approximately 22% of cells invaded the RBM and migrated through the filter in 6 hr. Seeding higher numbers of cells did not increase invasiveness at 6 hr. (Not shown.)

The cells were counted using an automated cell counter, such as the "COULTER MULTISIZER" made by Coulter, Inc. of Hialeah, Fla. By these experiments it was determined that an absorbance of 0.1 units of the crystal violet extract corresponds to approximately 5000 cells that migrated through the filter.

Similar procedures can be applied to calibrate the migration assay for other cells, to employ the assay to measure the therapeutic activity of other compositions of the present invention.

TABLE 1

| Relationship between cell invasion and optical absorbance | | | |
|---|---|---|---|
| Cells seeded ($\times 10^3$) | O.D. units[a] 585 nm) | Cells invading ($\times 10^1$) | Percentage invasion |
| 100 | $0.60 \pm 0.1$ | $31.8 \pm 0.2$ | $31.8 \pm 0.2$ |
| 200 | $1.50 \pm 0.2$ | $42.0 \pm 2.1$ | $21.2 \pm 1.0$ |
| 300 | $1.20 \pm 0.2$ | $72.3 \pm 2.7$ | $23.0 \pm 0.4$ |

[a]1 O.D. unit corresponds to approximately 5,000 cells.

Figure 2:
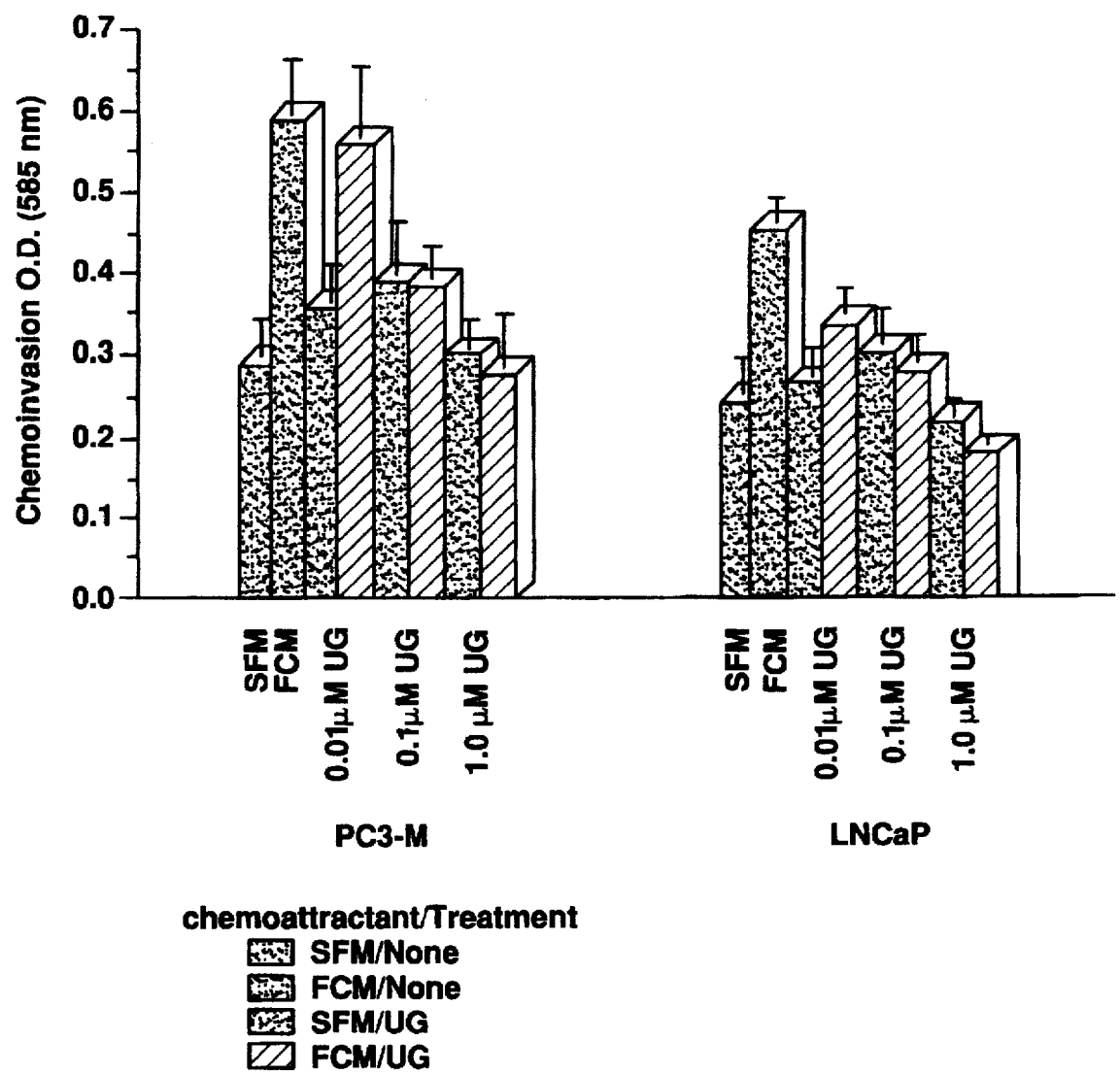
FIG. 2 is a bar chart showing the dose effect of uteroglobin on the invasiveness of cells of the PC3-M and LNCaP cell lines, epithelial cell lines derived from human prostate tumors. LNCaP cells are androgen-sensitive. PC3-M cells are androgen independent. Assays was performed as described in the caption to FIG. 1.

As shown in FIG. 1, cells of the TSU-Pr1 cell line exhibited the highest rate of basal invasiveness and the highest FCM-stimulated invasiveness. The basal rate for DU-145 cells was 2-fold lower than the rate for TSU-Pr1 cells, but the rate of stimulated invasiveness was comparable for the two cell lines. As shown in FIG. 2, basal and stimulated invasiveness of PC3-M cells both were 2-fold lower than that observed for DU-145 cells. (N.B. The scale change in FIG. 2.) LNCaP cells exhibited the lowest basal and the lowest stimulated invasiveness. FCM stimulation increased the invasiveness of this cell line 2–3-fold, also as shown in FIG. 2.

EXAMPLE 5

Uteroglobin inhibits invasiveness of tumor cells

The ability of uteroglobin to inhibit tumor cells invasiveness is illustrated by its effect on cells lines treated with 0.01, 0.1 or 1.0 µM uteroglobin. Each of the four cells lines was incubated for 24 hr. with these concentrations of uteroglobin. After the incubation period the cells were rinsed and then assayed for invasiveness. Inhibition of stimulated invasiveness then was quantitatively determined by subtracting the basal invasiveness from FCM-stimulated invasiveness, for each treatment group. Finally, the results were calculated as a percentage of the invasiveness of untreated control cells.

All four cell lines showed a dose-dependent inhibition of FCM-stimulated invasion, as shown in FIGS. 1 and 2, by the bars for FCM/UG. Notably, uteroglobin did not affect basal invasiveness, indicated by the bars labelled SFM/UG. Table 2 shows the average inhibition observed in three independent experiments, each of which was performed in triplicate. The inhibition of invasiveness by uteroglobin was found to be significant at the $P<0.01$ level for all conditions, except for PC3-M and TSU-Pr1 cells treated with 0.01 µM uteroglobin, which were significant at the $P<0.05$ level. As shown in Table 2, 1.0 μM uteroglobin inhibited invasiveness of DU-145 cells by 60%, PC3-M cells by 88%, LNCaP cells by 92% and the TSU-Pr1 cells by 59%.

TABLE 2

Inhibition of tumor cell invasiveness by uteroglobin
% Inhibition of invasion by uteroglobin

| Cell lines | 0.01 μM | 0.1 μm | 1.0 μM |
|---|---|---|---|
| DU-145 | 45.4 ± 6[a] | 49.9 ± 5[a] | 60.2 ± 11[a] |
| PC3-M | 43.4 ± 15[b] | 82.4 ± 14[a] | 87.9 ± 11[a] |
| TSU-Pr1 | 33.5 ± 10[b] | 44.4 ± 11[a] | 58.9 ± 8[a] |
| LNCaP | 71.5 ± 10[a] | 81.3 ± 6[a] | 92.3 ± 7[a] |

The table shows the results of assays described herein above. Briefly, tumor cells were cultured in media containing uteroglobin for 24 hr. and then assayed for invasive activity. Basal migration was subtracted and the adjusted measure is expressed as percent of untreated control cells for each cell type. Data is expressed as mean of three independent experiments performed in triplicate, and the variance is the standard error of the mean.

EXAMPLE 6

Time course of inhibition of invasiveness by uteroglobin

Figure 4:
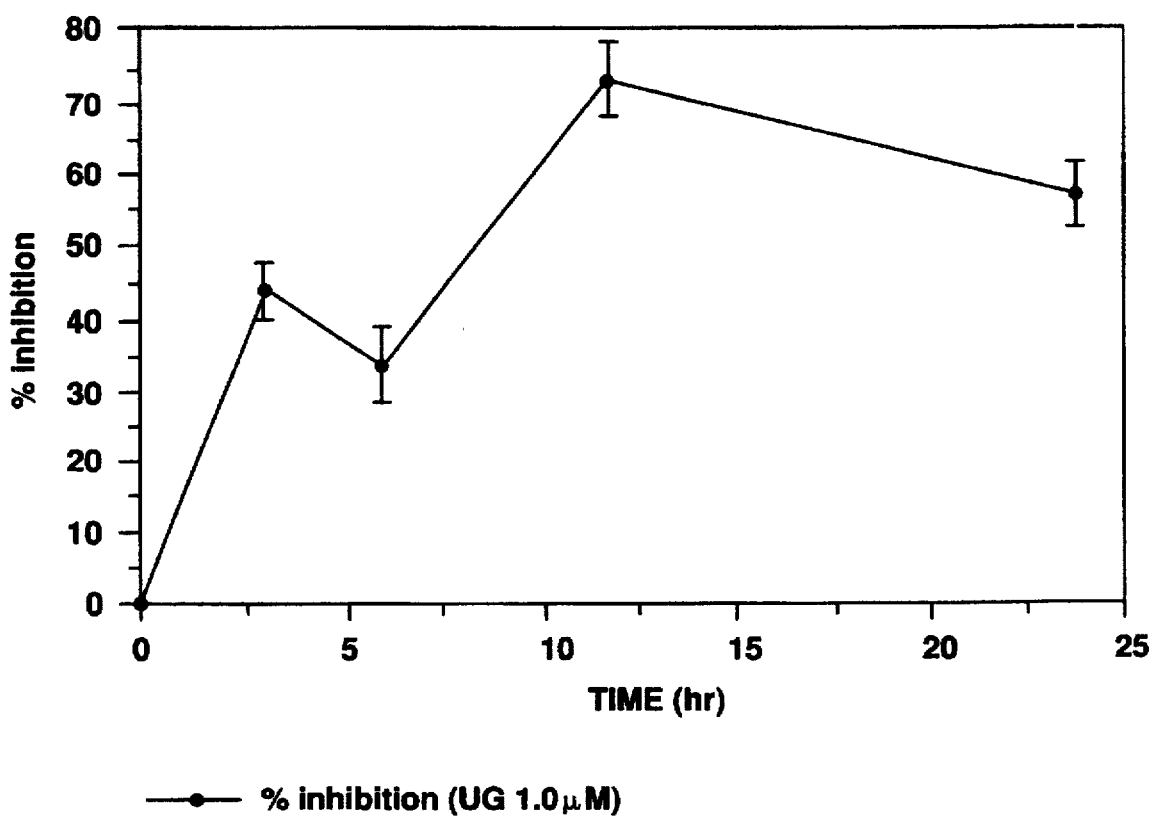
FIG. 4 is a graph showing a time course of the effect of uteroglobin on invasiveness of FCM-stimulated DU-145 cells. Cells were incubated without or with 1.0 μM uteroglobin for 3, 6 12, or 24 hr. and then assayed for invasion in response to FCM as described in the caption to FIG. 1.

The time course for suppression of invasiveness of DU-145 cells by uteroglobin was determined over a 24 hr. period. Cells were treated, as described above, for 3, 6, 12, or 24 hr. and then assayed for invasiveness. The maximum inhibition of invasiveness observed in the cells cultured in the presence of uteroglobin was 74%, at 12 hr. 50% maximum inhibition was observed after 3 hr., and at 24 hr. inhibition was 79% of the maximum. FIG. 4 shows these results is graphical form.

EXAMPLE 7

Uteroglobin does not affect motility, per se

Experiments were carried out to assess motility per se shows that uteroglobin does not affect cell motility, i.e., migration in the absence of RBM. The results show that uteroglobin specifically inhibits the invasion-associated motility of epithelial tumor cells. Invasion-associated motility, is implicated more specifically in metastasis than motility per se, involves the synthesis, recruitment, or activation of several different classes of proteolytic enzymes including collagenases, cathepsins, plasminogen activators and a variety of metalloproteinases required for degradation of basement membranes and the ECM. The observation that uteroglobin does not alter motility, but inhibits invasiveness, reflects the finding that uteroglobin does not inhibit basal invasiveness. The results show that uteroglobin specifically can inhibit invasiveness, without directly altering cell motility which may be an advantageous property for pharmacological intervention where non-specific effects of uteroglobin on normal motility could be disadvantageous.

EXAMPLE 8

Uteroglobin does not affect adhesion to RBM

The anti-invasive activity of uteroglobin is not mediated by an effect on cell adhesion. This can be seen from experiments in which the adhesiveness of DU-145 and PC3-M cells was measured after incubation for 24hr. in SM media or SM media containing 1.0 μM uteroglobin for 24 hr.

Adhesion was tested by removing the incubation media, resuspending the cells in fresh αMEM/SM, counting them, replating the cells and then counting the number of cells that had attached 1, 3 and 6 hr. after replating. The results show that uteroglobin does not alter adhesiveness of the cells. The absence of an effect of uteroglobin on basal migration, illustrated by the results depicted in FIGS. 1 and 2, supports the same conclusion.

EXAMPLE 9

Specificity of uteroglobin anti-metastatic effects

Figure 3:
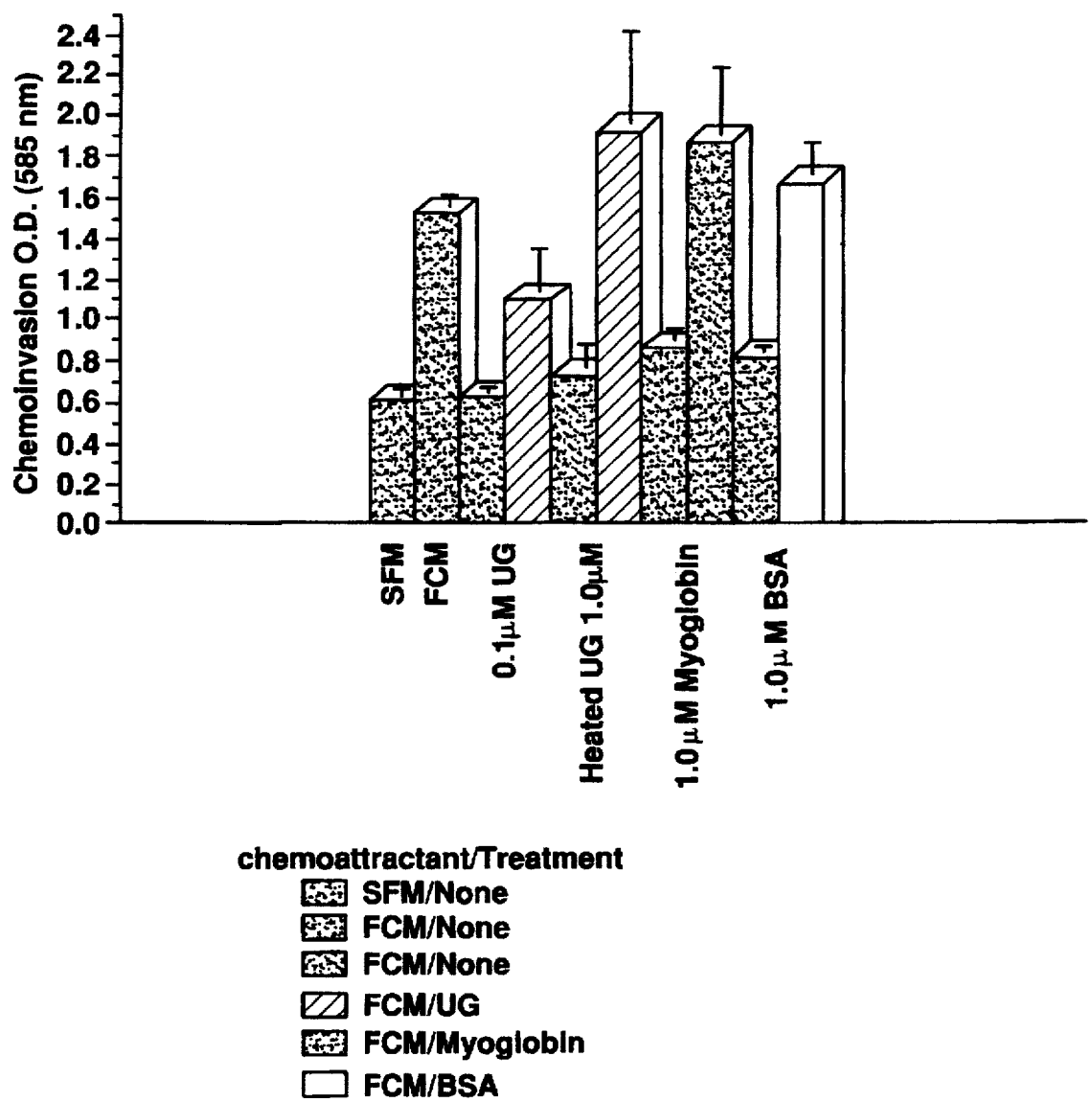
FIG. 3 is a bar chart showing that myoglobin, albumin and heat-inactivated uteroglobin do not affect the invasiveness of DU-145 cells.

The specificity of uteroglobin activity was demonstrated in DU-145 cells, using myoglobin, albumin and heat inactivated uteroglobin. Cells were treated for 24 hr with either myoglobin, albumin or uteroglobin that had been inactivated by incubation at 55° C. for 45 min. The results, presented in the graph in FIG. 3, show that myoglobin, albumin and heat-inactivated uteroglobin do not affect invasive activity of tumor cells.

EXAMPLE 10

Uteroglobin inhibits arachidonic acid release by FCM stimulated tumor cells

The effect of uteroglobin on the release of arachidonic acid ("AA") by tumor cells was assayed under conditions of basal and stimulated invasiveness. ($^{14}$C)AA having a specific activity 58.0 mCi/mmol was used to trace the arachidonic acid release. Labelled arachidonic acid of this type can be obtained from several commercial suppliers, such as Amersham, Inc. of Arlington Heights, Ill.

Uteroglobin inhibits release of arachidonic acid by DU-145 cells stimulated by FCM, as shown by the following experiment.

Intracellular arachidonic acid in DU-145 cells was labeled by incubating the cells in media containing $^{14}$C-labelled arachidonic acid. For this purpose approximately 0.75×10$^5$ cells were incubated for 24 hr. at 37° C. in 2 ml of α-MEM/SF media containing 1 μCi of ($^{14}$C)AA. After this, the cells were washed three times with 20 ml 0.2% bovine serum albumin to remove free radioactivity.

The washed, labelled cells were resuspended in 2 ml of α-MEM/SF, FCM or FCM containing 1.0 μM uteroglobin. Cells in each of the three media were incubated at 37° C. and 50 μl aliquots were removed of the media were removed from each culture 0.5, 10, 20 and 30 min., and 1, 2, 3, 4 and 5 hr. after the beginning of the incubation period.

Each aliquot was assayed for AA release, which was measured as $^{14}$C free in the media, determined by scintillation counting. Standard scintillents and counters were to quantitate radiation emission by $^{14}$C in the samples; e.g., EcoLite Biodegradable scintillant from ICN, Inc.

Stimulation of AA release by FCM was calculated by subtracting the amount of ($^{14}$C)AA released by cells incubated in αMEM/SF media (which was very low) from the amount of ($^{14}$C)AA released by cells incubated in FCM media. The effect of uteroglobin on FCM-stimulated AA release was calculated in the same way, by subtracting the amount of ($^{14}$C)AA released by cells cultured in αMEM/SF from the amount of ($^{14}$C)AA released by cells incubated in FCM containing 1 μM uteroglobin.

Figure 5:
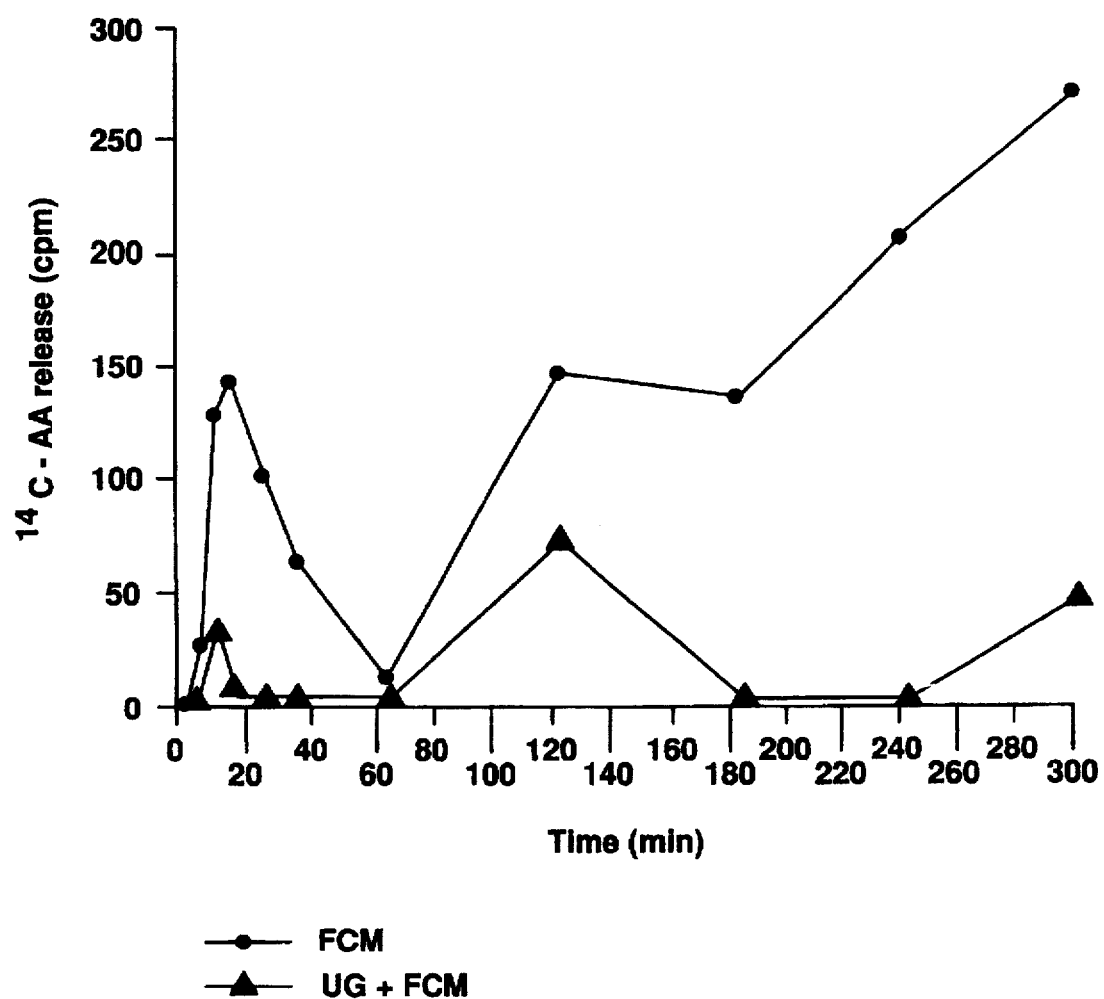
FIG. 5 is a graph showing that uteroglobin inhibits arachidonic acid release from FCM-stimulated DU-145 cells over a five hour period. Cells were incubated for 24 hr. in αMEM/SF media containing $^{14}$C-labelled arachidonic acid. Free label then was washed away, and the cells were incubated in FCM without and with 1 μM uteroglobin. Arachidonic acid release was measured by $^{14}$C released from the cells into the medium.

As shown in the graph in FIG. 5, arachidonic acid released by cells cultured in FCM media exhibited a biphasic profile. Released AA peaked at 20 min., the peak was followed by a period of reuptake, e.g. 60 min. and then there was a period of sustained release to the end of the 5 hr. incubation period of this experiment.

The presence of 1 μM uteroglobin in FCM media reduced FCM-stimulated release of arachidonic by 77% at 20 min. and 86% at 5 hr.

The dramatic inhibition of release of arachidonic acid by FCM-stimulated tumor cells, together with the foregoing results showing the inhibitory effect of uteroglobin on invasiveness, show that uteroglobin affects an early event in the signalling pathway(s) that control tumor invasiveness.

EXAMPLE 11

A patient presents with metastatic adenocarcinoma of the prostate. The adenocarcinoma appears not to have metastasized. The adenocarcinoma is removed by surgery. Uteroglobin is administered before and after surgery at a dose rate that reaches and then maintains a blood concentration of uteroglobin of approximately 1 µM. After post-operative recovery, the patient is maintained at a decreased level of uteroglobin by a regimen of periodic i.m. self-administration. No further occurrences of the adenocarcinoma develop.

EXAMPLE 12

A patient presents with metastatic adenocarcinoma of the prostate. The adenocarcinoma appears not to have metastasized. The adenocarcinoma is removed by surgery. Uteroglobin is administered before and after surgery, at a dose rate that reaches and then maintains a blood concentration of uteroglobin of approximately 1 µM. After post-operative recovery, the patient is maintained at a decreased level of uteroglobin by intermittent or continuous administration by subdural pump. No further occurrences of the adenocarcinoma develop.

EXAMPLE 13

A patient presents with metastatic adenocarcinoma of the prostate. The adenocarcinoma appears not to have metastasized. The adenocarcinoma is removed by surgery. Uteroglobin is administered before and after surgery, at a dose rate that reaches and then maintains a blood concentration of uteroglobin of approximately 1 µM. After post-operative recovery, the patient is maintained at a decreased level of uteroglobin by intermittent or continuous administration using a transdermal patch. No further occurrences of the adenocarcinoma develop.

EXAMPLE 14

A patient presents with metastatic adenocarcinoma of the prostate. The adenocarcinoma appears to have metastasized, but surgery still is indicated as an effective treatment modality. Tumor tissue is removed by surgery. Uteroglobin is administered from the time, approximately, of the initial diagnosis and continues after surgery, i.m. and i.v., at a dose rate that reaches and then maintains a blood concentration of uteroglobin above 1 µM. After post-operative recovery, the patient is maintained at this level of uteroglobin by a regimen of periodic i.m. self-administration. The patient is monitored carefully for intolerable adverse side-effects of high-dose uteroglobin administration. No further tumors develop.

EXAMPLE 15

A patient presents with metastatic adenocarcinoma of the prostate. The adenocarcinoma appears to have metastasized, but surgery still is indicated as an effective treatment modality. Tumor tissue is removed by surgery. Uteroglobin is administered from the time, approximately, of the initial diagnosis and continues after surgery, i.m. and i.v., at a dose rate that reaches and then maintains a blood concentration of uteroglobin above 1 µM. After post-operative recovery, the patient is maintained at this level of uteroglobin by a regimen of periodic i.m. self-administration. The patient is monitored carefully for intolerable adverse side-effects of high-dose uteroglobin administration. Although some of the original, small tumorous masses are detected after surgery, they do not grow in size.

EXAMPLE 16

A patient presents with metastatic adenocarcinoma of the prostate. The adenocarcinoma appears to have metastasized, but surgery still is indicated as an effective treatment modality. Tumor tissue is removed by surgery. Uteroglobin is administered from the time, approximately, of the initial diagnosis and continues after surgery, i.m. and i.v., at a dose rate that reaches and then maintains a blood concentration of uteroglobin above 1 µM. After post-operative recovery, the patient is maintained at this level of uteroglobin by a regimen of periodic i.m. self-administration. The patient is monitored carefully for intolerable adverse side-effects of high-dose uteroglobin administration. Tumorous masses are detected after surgery, but their growth is slowed.

EXAMPLE 17

A patient presents with a tumor of the breast, of epithelial cell origin. The tumor, which appears to be of a metastatic type, appears not to have metastasized. The tumor is removed by surgery. Uteroglobin is administered after surgery, i.m. and i.v., at a dose rate that reaches and then maintains a blood concentration of uteroglobin of approximately 1 µM. After post-operative recovery, the patient is maintained at a decreased level of uteroglobin by a regimen of periodic i.m. self-administration. No further occurrences of the tumor develop.

EXAMPLE 18

A patient presents with a breast tumor of epithelial cell origin. The breast tumor has metastasized. Numerous secondary tumors are detected. Insofar as possible, tumor tissue is removed by surgery. Surgical intervention is aggressive. Uteroglobin is administered from the time, approximately, of the initial diagnosis and continues after surgery, i.m. and i.v., at a dose rate that reaches and then maintains a blood concentration of uteroglobin above 1 µM. After post-operative recovery, the patient is maintained at this level of uteroglobin by a regimen of periodic i.m. self-administration. The patient is monitored carefully for intolerable adverse side-effects of high-dose uteroglobin administration. No further tumors develop in the remaining breast or elsewhere in the body.

What is claimed is:

1. A method for preventing or inhibiting metastasis of a cancer of epithelial cell origin, comprising the step of administering uteroglobin to an organism suffering from a cancer of epithelial cell origin wherein the uteroglobin inhibits arachidonic acid release by cells of said cancer and where the step of administering is by a route and in an amount effective to inhibit or prevent metastasis of said cancer without administering anti-angiogenesis agents.

2. The method according to claim 1, wherein said compound is human uteroglobin.

3. The method according to claim 1, wherein said cancer is a cancer of the prostate gland in a human patient.

4. The method according to claim 1, wherein said method is used in conjunction with an additional treatment, excluding anti-angiogenesis agents.

5. The method according to claim 4, wherein said additional treatment is surgical intervention, radiation therapy, hormonal therapy, immunotherapy, chemotherapy or cryotherapy, excluding anti-angiogenesis agents.

6. A pharmaceutical composition for inhibiting or preventing metastasis of a cancer of epithelial cell origin in an organism, comprising:
  (i) uteroglobin wherein the uteroglobin inhibits arachidonic acid release by cells of the cancer of epithelial cell origin;
  (ii) an additional agent used in combination with the composition, wherein said additional agent is selected from the group consisting of chemotherapeutic agents, ablation or therapeutic hormones, antineoplastic agents, monoclonal antibodies, and radioactive agents;
  iii) a carrier for effective therapeutic administration of said composition to said organism; and
  iv) excluding anti-angiogenesis agents.

7. The composition according to claim 6, wherein said cancer is a cancer of the prostate gland in a human patient.

8. The composition according to claim 6, wherein said compound is human uteroglobin.

* * * * *